United States Patent [19]
Allen et al.

[11] Patent Number: 6,077,621
[45] Date of Patent: Jun. 20, 2000

[54] METHOD OF FORMING ROBUST METAL, METAL OXIDE, AND METAL ALLOY LAYERS ON ION-CONDUCTIVE POLYMER MEMBRANES

[75] Inventors: Robert J. Allen, Saugus; James R. Giallombardo, Beverly, both of Mass.

[73] Assignee: De Nora S.p.A., Italy

[21] Appl. No.: 09/003,228

[22] Filed: Jan. 6, 1998

Related U.S. Application Data

[60] Provisional application No. 60/035,999, Jan. 22, 1997.

[51] Int. Cl.⁷ ................................................... H01M 4/02
[52] U.S. Cl. .............................. 429/33; 429/29; 429/40; 429/46; 134/1; 134/1.2; 134/1.3; 427/38; 427/39; 204/192.14
[58] Field of Search ............................ 429/30; 427/38; 134/1, 33; 156/643; 361/504

[56] References Cited

U.S. PATENT DOCUMENTS

| | | | |
|---|---|---|---|
| 4,277,147 | 7/1981 | Arnoldussen | 350/357 |
| 4,278,493 | 7/1981 | Petvai | 156/643 |
| 5,032,421 | 7/1991 | Sarma | 427/38 |
| 5,631,099 | 5/1997 | Hockaday | 429/30 |
| 5,652,044 | 7/1997 | Rickerby | 428/216 |
| 5,748,438 | 5/1998 | Davis | 361/504 |
| 5,750,013 | 5/1998 | Lin | 204/192.14 |
| 5,849,093 | 12/1998 | Andra | 134/1 |

*Primary Examiner*—Maria Nuzzolillo
*Assistant Examiner*—Mark Ruthkosky
*Attorney, Agent, or Firm*—Bierman, Muserlian and Lucas

[57] ABSTRACT

The invention is to a dual beam process for providing an ion-conducting membrane with a thin metal or metal-oxide film. The process includes the cleaning of a membrane surface with a low energy electron beam followed by the deposition of the metal or metal-oxide film by a high energy electron beam of ions.

15 Claims, 1 Drawing Sheet

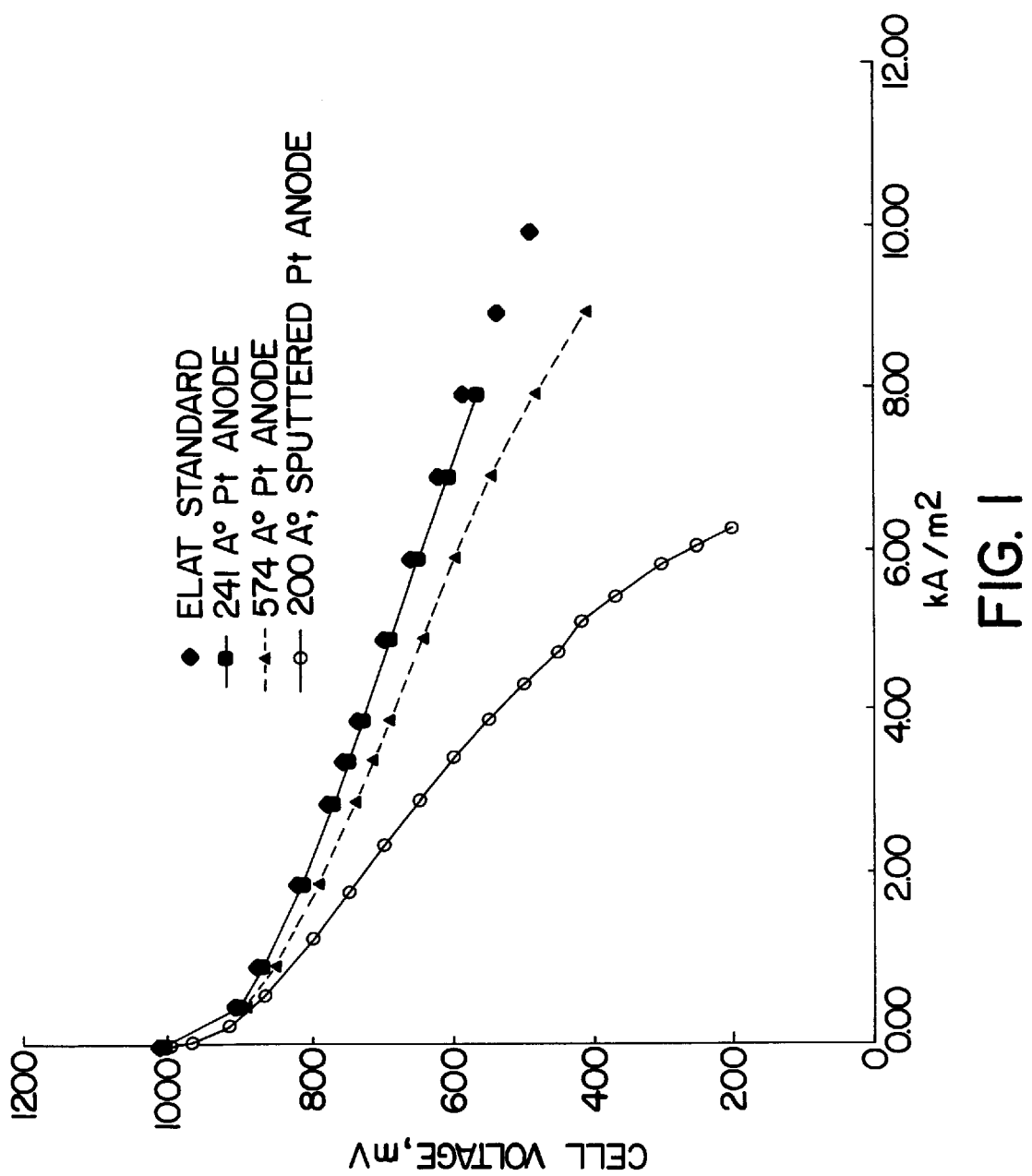

METHOD OF FORMING ROBUST METAL, METAL OXIDE, AND METAL ALLOY LAYERS ON ION-CONDUCTIVE POLYMER MEMBRANES

This application claims priority to provisional application Ser. No. 60/035,999, filed Jan. 22, 1997.

BACKGROUND

This invention relates to a new method to coat metals, metal oxides, or metal alloys onto solid polymer electrolytes or other ion-conducting polymer surfaces. Materials prepared using this method would gain advantage in electrochemical and membrane-based applications. By employing dual ion-beam assisted deposition (IBAD), one can systematically prepare consistent thin films of these metals on solid polymer electrolyte membranes such as Nafion® (DuPont, Wilmington, Del.), a copolymer of tetrafluoroethylene and sulfonyl fluoride vinyl ether and the membranes coated thereby and electrolytic cells containing the same.

STATE OF THE ART

The use of solid polymer electrolytes has greatly expanded the field of electrochemistry. Electrochemical processes depend on the transfer of ionic and electronic charge through the use of an anode, cathode, and an ionic liquid electrolyte. However, with the advent of the solid polymer electrolyte fuel cell, the traditional liquid phase has been replaced with a membrane composed of a polymer electrolyte that transfers ionic charge under typical electrolytic conditions. These solid polymer electrolytes are often ion-conducting membranes that are commercially available. For example, in addition to the previously mentioned Nafion (a cation exchange membrane), Asahi Chemical and Asahi Glass make perfluorinated cation exchange membranes whereby the ion exchange groups(s) are carboxylic acid/sulfonic acid or carboxylic acid. These companies produce cation exchange membranes with only the immobilized sulfonic acid group as well. Non perfluorinated ion exchange membranes are available through Raipore (Hauppauge, N.Y.) and other distributors such as The Electrosynthesis Co., Inc. (Lancaster, N.Y.). Anion exchange membranes typically employ a quaternary amine on a polymeric support and are commercially available as well. Other manufacturers and researchers fill the pores of an inert matrix with immobilized ionomer, creating an effective ion conducting membrane. (For example, see Fedkiw, P. S. and Nouel, K. M. in *Electrochemica Acta,* 1977).

Nafion is typically employed in some fuel cells. For the hydrogen/air ($O_2$) fuel cell, hydrogen and oxygen are fed directly to the anode and cathode respectively, and electricity is generated. In order for these "gas breathing" electrodes to perform, the electrode structure must be highly porous to allow three phase contact between the solid electrode, the gaseous reactant, and the electrolyte, which can be in the form of a membrane or polymer electrolyte. This class of electrode is called a gas diffusion electrode. In addition to a gaseous hydrogen fuel and gaseous air ($O_2$) oxidant, others employ a mixed phase system such as the methanol/air ($O_2$) fuel cell. Here, liquid methanol is oxidized at the anode while oxygen is reduced at the cathode. Another utilization for ion-conducting membranes and gas diffusion electrodes includes the electrochemical generation of pure gases (for example see Fujita et al in *Journal of Applied Electrochemistry,* vol. 16, page 935, (1986)), electro-organic synthesis (for example see Fedkiw et al in *Journal of the Electrochemical Society,* vol. 137, no. 5, page 1451 (1990)), or as transducers in gas sensors (for example See Mayo et al in *Analytical Chimica Acta,* vol. 310, page 139, (1995)).

Typically, these electrode/ion-conducting membrane systems are constructed by forcing the electrode against the ion conducting membrane. U.S. Pat. Nos. 4,272,353; No. 3,134,697; and 4,364,813 all disclose mechanical methods of holding electrodes against the conducting membrane. However, the effectiveness of a mechanical method for intimately contacting the electrode to the polymer membrane electrolyte may be limited since the conducting membrane can frequently change dimensions due to alterations in hydration and temperature. Swelling or shrinking can alter the degree of mechanical contact.

Thus, a preferred method of contacting the electrodes with the polymer membrane electrolyte involves direct deposition of a thin electrode onto one or both sides of the polymer substrate. Nagel and Stucki in U.S. Pat. No. 4,326,930 disclose a method for electrochemically depositing platinum onto Nafion. Others have employed chemical methods whereby the metal salt is reduced within the polymer membrane (for example see Fedkiw et al in *Journal of the Electrochemical Society,* vol. 139, no. 1, page 15 (1992)). In both the chemical and electrochemical methods, one essentially precipitates the metal onto the ion conducting membrane. This precipitation can be difficult to control due to the nature of the ion-conducting polymer membrane, the form of the metal salt, and the specific method employed to precipitate the metal. As the goal of a thin, porous, and uniform metal layer is often not met via precipitation, practitioners have turned to other deposition methods.

Scientists and engineers have long realized that the specialized coating methods of ultra-high vacuum (UHV) evaporation, chemical vapor deposition (CVD), and sputter deposition (also called sputtering), may offer a better method to create thin metal electrode surfaces. A successful surface treatment via UHV starts with creating a clean substrate. Insuring the substrate surface is atomically clean before deposition can be of vital importance for adhesion. A source metal is contained in a water cooled copper hearth. This metal is vaporized through resistive, eddy-current, electron bombardment, or laser heating. The resulting vaporized metal diffuses to the substrate and condenses to form a film. Evaporation rates depend exponentially on temperature and thus means for precise temperature control is needed.

One method for minimizing these control problems is to heat the substrate to a temperature that still allows for condensation of the vapor. UHV is often used when freedom from contamination in both the film and the interface between the film is of the utmost importance—for example in the electronics industry. While UHV is appropriate for modifying electrode surfaces, using this technique for the direct deposit of a thin electrode layer onto an ion-conducting polymer substrate may be limited due to the temperature of deposition and constraints of an atomically clean substrate.

The chemical vapor deposition process occurs at atmospheric pressure and typically employs temperatures lower than UHV or sputtering. In CVD, the constituents of a vapor phase are often diluted with an inert carrier gas. The carrier and vapor phase are reacted at a hot surface and subjected to ions created by circular magnetrons. The substrate target is not part of the ion-creating circuit so only neutral vapors are deposited onto the target. However, unlike the condensation of UHV and sputtering, the surface reaction for CVD is considered a chemical reaction. For example, to deposit tungsten, one would mix hydrogen with tungsten hexafluoride at 800° C. Tungsten metal then deposits on the substrate via diffusion. While CVD may offer a potential method to coat an ion-conductive polymer membrane, once again the temperature restraints may allow this technique only limited application.

The most common metal deposition method is sputtering. The process begins by mounting a sample to a water-cooled support. The sample is next subjected to a vacuum, although not as high as in the UHV technique. Once vacuum is achieved, a source of metal is heated until the metal vaporizes. These metal atoms are further bombarded by positive ions of a carrier gas. The now ionized metal atoms diffuse to the substrate. Since the sample is cooled, the resulting metal vapor condenses on the sample. However, continuous ion bombardment imparts enough energy to re-evaporate the deposited metal on the substrate.

This annealing process of bombardment, condensation, and additional evaporation from the substrate eventually forms a thin metallic film. The pressure and substrate temperature employed controls the morphology of film formation. Often, substantial heating of the substrate occurs as the sputtered ions cool and evaporative energy is transferred to the substrate. Substrate heating is especially problematic when metal with high ejection energies are employed (platinum, tungsten, tantalum, rhenium, and uranium). Excessive heating can cause distortion in the film through differential expansion between the film and substrate. For this reason, sputtered films of platinum on Nafion are not stable: the difference in thermal capacity between the two materials is too great.

Regardless, the necessity to construct thin layers of electrodes has led researchers to coat anodes or cathodes. Sputtering has been employed to make fuel cell type electrodes by depositing a thin layer of metal onto a carbon support and not directly on the ion-conducting polymer membrane. Weber et al show in *The Journal of the Electrochemical Society* (vol 134, no. 6, page 1416, 1987) that platinum can be successfully sputtered onto carbon composite electrodes, and the performance of these electrodes in an alkaline (liquid) fuel cell is comparable, if not better than traditional methods of preparation. Aside from performance, there is an advantage in being able to use lower amounts of platinum without extensive loss in performance, thus reducing the cost of the composite.

Ion-conducting polymer membranes are often used as selective separators in electrolytic processes. For example, Nafion is a cation exchange separator employed in brine electrolysis. Sodium ions from brine migrate through the separator to combine with hydroxide formed at the cathode. Chloride ions remain in the anolyte compartment due to charge repulsion with the immobilized sulfonic acid groups of the Nafion. Other uses of charged membranes for separation include electrodialysis and synthesis. For most of these applications, it is desired to transport one species at the exclusion of others. However, ion-exchange separators do not always perform as desired. For example, the previously cited methanol/oxygen fuel cell suffers from unwanted transport of methanol through the ion-conducting separator. In addition to protons, the separator allows methanol to cross over to the oxygen-reduction side, eventually parasitically reacting at the cathode, thereby lowering the cathode potential.

It is known that thin coatings of certain metals, metal oxides, or alloys selectively allow the transport of ions. For example, thin layers of palladium, tungsten oxide, molybdenum oxide or hydrogen uranyl phosphate ($HUO_2PO_4$) have been shown to selectively transport protons. If a thin layer of these or other metals could be securely fixed to an ion-conducting membrane, then one would expect enhanced selectivity for ion transport.

Thus, if one were able to coat ion-conducting membranes with a thin, robust metal, metal oxide, or alloy layer, one would accrue performance and cost advantages in both electrochemical and separation applications. As individual techniques, the current metal deposition technologies (UHD, CVD, sputtering) are limited in their ability to generally apply a thin metal film to an ion-conductive membrane due to either operating temperatures or process conditions.

DESCRIPTION OF THE INVENTION

The novel process of the invention for the preparation of an ion-conducting membrane provided with a thin film of a metal deposited thereon comprises subjecting under vacuum the membrane to a low energy electron beam which cleans the membrane surface and then subjecting under vacuum the cleaned membrane to a high energy electron beam containing metal ions to form a thin metal film on the membrane useful as an electrode-membrane structure. The resulting metallized membrane structures and fuel cells containing the same are also novel and part of the invention.

The metal-membrane electrodes can be used in fuel cells such as described in U.S. Pat. No. 4,044,193 or hydrogen-reduction metal recovery cells described in U.S. Pat. No. 4,331,520 or gas diffusion cells as described in U.S. Pat. No. 5,047,133.

Dual ion-beam assisted deposition (Dual IBAD) is a hybrid method that combines some of the best features of the above metal deposition technologies. Using both a vacuum and temperature control, IBAD combines vapor deposition with simultaneous ion-beam bombardment. The vapor deposition is initiated via electron-beam evaporation of the source. Along with the evaporated species, two ion-beams converge on the substrate. A relatively low energy source of ions is initially focused on the substrate. Typical low energy ion beams are $Ar^+$. This first beam both cleans the surface through ion-sputtering and in some cases imparts a unique atomic-scale texture to which the coating will be applied.

The second, higher energy beam, e.g. $O_2^+$ or $N_2^+$, and the electron-evaporated species (e.g. platinum, iridium, gold, rhenium, rhodium, tantalum, tungsten, silver, zinc, iron, copper, nickel, etc.) are aimed at the surface. It is believed that the concurrent ion stitching densifies the now forming film and improves the adherence between the film and the substrate.

In some cases the energy of the two energy beams is identical, and the ion carrier is a single gas. This variation is simply called IBAD. The use of Dual IBAD versus IBAD is determined by the peculiarities of the alloy, metal, or metal oxide source target and the polymer substrate to be coated.

The use of the concurrent ion beams allows one to construct adherent films of highly controlled porosity, depth, and ion composition on a variety of materials. For example, IBAD has been used to deposit metal, metal oxide, metal alloy, or metalloid films on metals, ceramics, or insulating polymers such as silicone rubber and polyimide. By adjusting deposition parameters, a film's porosity can be controlled and range from being highly dense and impervious (for example as a thin coating to create ion-selective membranes) to highly porous (a desirable quality for gas diffusion or fuel cell electrodes). Also, different metals, metal oxides, metalloid, or alloys can be constructed and deposited on the substrate at the atomic level. Typical coating times are 5 minutes per square meter: the process can be adapted to a semi-continuous drum feed whereby large quantities of material can be coated at once.

One key to the IBAD process as a general coating procedure is that the method functions over a wide range of temperature and pressure conditions. The essential attributes of the IBAD process are as follows:

It is a low temperature process which can be used on any substrate material.

It results in excellent adhesion of metallic or ceramic films on metal, polymer membranes, or ceramic substrates.

One can form dense, low-stress metal films with a porous or non-porous structure.

Superb control over film microstructure and chemical composition.

Scaleable, economic process.

IBAD conditions are dependent on the chemistry of the substrate to be coated and the ionization of the target metal and ion beam gas. For example, if ultra-high purity "zero defect" depositions are desired, then very high vacuums are employed, on the order of less than or around $10^{-10}$–$10^{-12}$ torr.

The temperature employed is both dependent on the substrate and the chemistry of deposition. However, for IBAD, the temperature does not affect the process as much as the material characteristics of the polymer substrate. For example, for Nafion® type polymer substrates, one could employ a range equal or less than 80–160° C., but preferably less than 80° C. If one is coating a Teflon type polymer, a temperature range of 50–250° C. is acceptable, but in all cases below 300° C. One prefers to operate below the glass-transition point of the polymers.

The energy of the high and low power ion beam is dictated by both the gas employed, and ultimately (for the high power) by the power available to the instrument. Typical low power beams range from 100–500 eV while high power beams range from 500–2000 eV.

The IBAD methodology has been exploited to coat ion-conducting membranes and create electrode and membrane structures of far greater film adhesion and interface control than previously possible. Porous electrode-membrane structures created via IBAD have a primary use as gas diffusion and find immediate implementation in fuel cell, electrosynthetic, sensor, and electrochemical separation fields. However, since thin, dense, and impervious films can also be formed on ion-conducting membranes, metal membrane structures find use as highly selective separators. For example, the problem of methanol cross-over and reactions at the cathode in a methanol/oxygen fuel cell may be alleviated by depositing a thin impervious layer of tungsten oxide on the ion-conducting membrane. The tungsten oxide would allow the passage of protons while isolating methanol from the cathode reaction.

In another facet of the invention, the process may be used for coating a gas diffusion electrode that has had a layer of ionomer applied to its surface prior to the IBAD treatment. This alternate ionomer layer would be like an in situ membrane.

Typically these liquid ionomers are obtained as solutions and can be thermally or chemically treated to form a thin film. For example, Nafion solution can be purchased as a 5% (wt) solution in isopropyl alcohol and other solvents whereby the equivalent weight of the polymer is 1100. This solution is sprayed or painted onto an uncatalyzed ELAT™, and heated at 80° C. to form a polymeric layer on the electrode. IBAD could then be employed to coat metals, alloys, or metal oxides on the ion conducting polymer layer. Structures formed in this manner can still be mated to a standard ion conducting membrane as well. Thus, a complete electrode pair would consist of the following layers:

ELAT/Nafion (from sln)/IBAD-metal/Nafion(memb.)/IBAD-metal/Nafion (from sln.)/ELAT "IBAD-metal" designates an ion beam assisted deposition of a layer of metal, alloy, or metal oxide.

As a new process for constructing a metal, metal oxide, or alloy interface on an ion-conducting membrane, many benefits are obvious. The cost for creating electrodes or membranes is expected to be significantly reduced as all of the deposition process is automated. The throughput of structures created through IBAD is expected to be as fast or faster than the current labor-intensive techniques. Finally, the ability to tailor the surface and interface of the metal ion-conducting structure to the demands of a specific application without significantly altering the actual manufacturing process allows for short development times of custom fabricated structures.

In the following examples, there are described several preferred embodiments to illustrate the invention. However, it should understood that the invention is not intended to be limited to the specific embodiments.

EXAMPLE I

The following example demonstrates the use of an IBAD-prepared gas diffusion electrode in a hydrogen/air ($O_2$) fuel cell. A sample of Nafion 115 (8"×8") is used as received except for wiping the surface clean with a soft tissue before placing it on a drum. The drum was rotated at 2.5 rpm throughout the process and the system was evacuated to $10^{-6}$ torr. The metal source target was platinum while argon was ionized in both the energy beams. The energy of the beams was between 200 and 1000 eV. A source of platinum was the target for an evaporation electron beam powered with a 14K watt supply. The incipient platinum film's progress was monitored via quartz crystallometer. The sample temperature was monitored and ranged from 35 to 65° C. For this trial, one side of the Nafion was coated with platinum. Four samples were prepared whereby the average film thickness was 3000, 1000, 574, and 241 angstroms. The assemblies with 574 and 241 angstrom platinum films were judged sufficiently porous to run as gas diffusion electrodes.

The hydrogen/air ($O_2$) fuel cell test stand consisted of a single anode/cathode pair of 16 $cm^2$ exposed electrode area. Appropriate hardware fed oxygen or air ($O_2$) to the cathode at 4 bar while hydrogen was supplied to the anode at 3.5 bar. In this test, air provided a source of oxygen and the cell temperature was maintained to 70° C. A current load ranging from 0–10 $KA/m^2$ was applied to the cell and a resulting steady-state voltage was recorded.

The evaluation consisted of testing three configurations of electrode. As a control, the cell was assembled with two standard commercially-available gas diffusion electrodes pressure-fit against an ion-conducting membrane (Nafion 115). An ELAT™ platinum gas diffusion electrode (E-TEK, Inc., Natick, Mass.) was employed as both the anode and cathode in this configuration. The second configuration replaced the Nafion membrane and ELAT anode with a single platinum-Nafion assembly whereby the platinum layer was 241 angstroms. The last configuration consisted of a similar anode assembly except the platinum layer was 574 angstroms. In all these configurations, no additional Nafion paint was applied to the metal coated membrane or ELAT as is sometimes cited in the literature. For all of these configurations, air ($O_2$) was fed to the cathode.

COMPARATIVE EXAMPLE

This example illustrates the difference between the structures formed when typical sputtering methodology is employed to coat ion exchange membranes such as Nafion. A sample of Naftion 115 (8"×8") was used as received except for wiping the surface clean with a soft tissue before placing on a drum. The sample was subjected to a vacuum applied to a sputtering chamber and a target of platinum was evaporated at high energy, and vaporized platinum condensed on the Nafion. The sputtering was halted once an approximately 200 angstrom film was formed. Samples of Nafion thus prepared were tested as anodes and cathodes in a fuel cell set-up previously described in Example 1.

The resulting metal film adhered tightly to the Nafion membrane and, even upon exposure to water, the metal film remained intact. However, as shown in FIG. 1, the electrochemical performance of such a structure was sub-standard. FIG. 1 also plots the results of a sputtered platinum anode on the same axis as the standard electrode and IBAD prepared electrodes. It is readily apparent from this plot that the current and voltage obtained from the sputtered metal film was far below the IBAD or standard electrodes. This shows that the sputtering process leads to metal film deposits with undesirable morphological characteristics.

DESCRIPTION OF THE FIGURE

FIG. 1: A current potential plot of four fuel cell trials. The single cell is run with hydrogen (3.5 bar) and air ($O_2$) (4 bar) while the temperature is maintained at 70° C. In all cases Nafion 115 is employed. The cathode-anode pair consisted of either an ELAT-ELAT, ELAT-241 Å IBAD platinum, ELAT-574 Å IBAD platinum, or 200 Å sputtered platinum. All experimental electrodes are run as anodes while the cathode is the same material.

This example illustrates that gas diffusion electrodes made with IBAD can perform as well as assemblies currently commercially available. An ELAT is a carbon-cloth based support onto which carbon and hydrophilic wet-proofing layers are applied to both sides and whereby the platinum catalyst is similarly applied by hand. In contrast, the IBAD electrode is made with a minimum of labor, and as shown employs far greater utilization of the applied platinum by using less platinum. Moreover, the metal-membrane electrodes of the invention have much improved cell voltages.

EXAMPLE II

This example demonstrates the use of IBAD—modified ion conducting membrane as a highly selective separator. The problem of methanol crossover in a direct methanol fuel cell (DMFC) can be alleviated if a thin, dense, and impervious film is created on an ion-exchange membrane whereby protons are selectively transported through the structure. Such an assembly thus allows methanol oxidation at the anode, migration of the resulting protons through the structure, and oxygen reduction at the cathode whereby the protons re-combine with the oxygen reduction production to form water.

Tungsten oxide is a known selective proton conductor. However, previously known methods to form thin, impervious films of this oxide on an ion conductive membrane have precluded its use in the DMFC, or other applications.

Thin films of tungsten trioxide were formed on 8"×8" pieces of Nafion. As in the previous example, the Nafion was mounted on a drum after a simple tissue wiping. The drum was rotated from 2 to 5 rpm throughout the process. The sample chamber was evacuated to $10^{-6}$ torr. and the metal source was electronic grade $WO_3$. A single beam was employed to assist in the ion deposition (i.e. "IBAD"). Argon was the ion carrier for the ion beam and the energy for the deposition beam ranged from approximately 100 to 1000 eV. The tungsten oxide source was vaporized with an evaporation electron beam powered by a 14K watt supply. Using this supply, the source metal was evaporated at a coating rate of 3–10 Å/s. Formation of the metal oxide film was monitored via a quartz crystallometer and the sample temperature was below 100° C. at all times. Since the objective was to form a selective barrier, only one side of the ion-conductive membrane was coated. Two thicknesses were prepared: 0.45 and 1.05 microns. (4,500 and 10,500 Å).

Prior to testing the modified Nafion, a membrane electrode assembly (MEA) was constructed. The Los Alamos "decal" method was employed to affix platinum or platinum-ruthenium oxide electrodes to both the side with the tungsten oxide film and the unmodified side. More details in the method are described in *Proton Conducting Membrane Fuel Cells* 1. S. Gottesfeld et al, The Electrochemical Society, Pennington, N.J., Oct. 95, p. 252.

The primary assembly steps are described here. Anode and cathode inks were prepared by dispersing catalyst powders in an alcoholic solution of Nafion ionomer (5% wt. Solution, EW=1100). The anode ink catalyst was created from platinum-ruthenium oxide while the cathode was platinum black. The inks were painted onto a 5 $cm^2$ Teflon blank and oven dried. In this example, the tungsten oxide film was on the membrane side that ultimately served as the anode. A Teflon blank was pressed against the cathode (uncoated) side of the Nafion at a pressure of 2000 psi for 2 minutes while maintaining a temperature of 125° C. The anode ink consisting of platinum ruthenium oxide was painted onto carbon cloth gas diffusion media (ELAT™ from E-TEK Inc., Natick, Mass.) and this carbon blank is then pressed to the tungsten oxide at 125° C. and 200 psi for 2 minutes. The resulting electrodes contained an anode metal loading of 2–3 mg/$cm^2$ while the cathodes contained a metal loading of 2–3 mg/$cm^2$ of platinum black.

A single cell consisting of a 5 $cm^2$ active electrode area was assembled and placed in the test apparatus. A standard hydrogen/air and hydrogen/oxygen gas mix was fed to condition and obtain baseline data for the cell. Next, a 1 M MeOH solution was fed to the cell at 2 ml/min while oxygen was fed to the cathode at 400 ml/min and 60 psi while the system was held at 80° C.

Monitoring the cathode outlet for carbon dioxide with an infrared spectrometer allowed one to quantitate methanol crossover. The amount of $CO_2$ was then used to calculate a methanol flux value, which was then used to calculate an effective methanol crossover current. The methanol crossover current was the loss of cell current due to the undesirable transport of methanol through the membrane to the cathode. Large values of mA/$cm^2$ indicated poor cell performance. In addition to taking polarization curves, the cell was subjected to high frequency AC-impedance experiments whereby the effective resistance of the membrane was determined. The results for the 0.45 micron tungsten oxide are summarized in Table 1 below.

TABLE 1

Summary of DMFC with Tungsten Oxide Selective Barrier

| Measured Quantity | .45 microns film on Nafion 115 | Unmodified Nafion 115 |
|---|---|---|
| High Frequency Resistance $\Omega\ cm^2$ | 0.14 | 0.14 |
| Methanol Cross-over Current | 93–110 | 150–160 |

Examination of Table 1 shows that the transport of methanol had decreased approximately 31% by using the tungsten oxide modified Nafion. Furthermore, and just as important, the conductivity of the Nafion did not decrease. The functional nature of tungsten oxide was preserved, as the suboxides were considered both ionically and electronically conductive. This example demonstrates that IBAD can be employed to create selective barriers. In this case, proton transport was maintained while unwanted methanol transport was inhibited.

While the current and prior examples illustrate the key idea of ion assisted deposition, they serve as illustrations and do not intend to limit the application to only IBAD. Dual IBAD is applicable in certain circumstances. Similarly, the use of two or more separate metal or metal oxide targets is possible, allowing the formation of binary or trinary valve or platinum groups, metal alloys such as Pt:Ru, Pt:Sn, Pt:Mo, Pt:Rh, Pt:Ir, Pt:Pd, Rh:Mo, Pt:Co:Cr, Pt:Co:Ni, etc. directly on the ion conducting membrane.

Various modifications of the process and products of the invention may be made without departing from the spirit or scope thereof and it is to be understood that the invention is intended to be limited only as defined in the appended claims.

What we claim is:

1. A dual beam assisted deposition process for the purpose of an ion-conducting membrane provided with a thin metal or metal oxide film comprising subjecting the ion-conductive membrane under vacuum to an electron beam having an energy less than 500 eV to clean the membrane surface and subjecting the cleaned membrane under vacuum to a beam having an energy between 500 to 2000 eV and containing ions of the metal to be deposited to form the metal or metal oxide film.

2. The process of claim 1 wherein the metal to be deposited is platinum.

3. The process of claim 1 wherein the metal oxide to be deposited is tungsten oxide.

4. The process of claim 1 wherein the metal to be deposited is an alloy of platinum group metals.

5. A metallized membrane structure produced by the process of claim 1.

6. The membrane of claim 5 wherein the metal film is highly porous.

7. The membrane of claim 5 wherein the metal film is highly dense and impervious.

8. The membrane of claim 5 wherein the metal or metal oxide is a platinum group metal.

9. The membrane of claim 8 wherein the metal is platinum.

10. The membrane of claim 8 wherein the metal oxide is tungsten oxide.

11. In a fuel cell with an anode and a cathode separated by an ion-conductive membrane, the improvement consisting of using a membrane of claim 5 as the anode-membrane.

12. The fuel cell of claim 11 wherein the membrane is provided with a platinum metal film.

13. The fuel cell of claim 11 wherein the membrane is provided with a tungsten oxide film.

14. In a process of oxidizing methanol at the anode and reducing oxygen at the cathode in a fuel cell, the improvement comprising using the fuel cell of claim 11 wherein the film is impervious to methanol transport.

15. The process of claim 14 wherein the film is tungsten oxide film.

* * * * *